(12) United States Patent
Umebayashi

(10) Patent No.: US 10,058,459 B2
(45) Date of Patent: Aug. 28, 2018

(54) DISPOSABLE WORN ARTICLE AND METHOD FOR PRODUCING SAME

(71) Applicant: Toyoshi Umebayashi, Osaka (JP)

(72) Inventor: Toyoshi Umebayashi, Osaka (JP)

(73) Assignee: ZUIKO CORPORATION, Osaka (JP)

(*) Notice: Subject to any disclaimer, the term of this patent is extended or adjusted under 35 U.S.C. 154(b) by 303 days.

(21) Appl. No.: 14/877,385

(22) Filed: Oct. 7, 2015

(65) Prior Publication Data

US 2016/0022506 A1 Jan. 28, 2016

Related U.S. Application Data

(62) Division of application No. 13/806,791, filed as application No. PCT/JP2011/066328 on Jul. 19, 2011, now abandoned.

(30) Foreign Application Priority Data

Aug. 5, 2010 (JP) .................... 2010-176209

(51) Int. Cl.
*A61F 13/49* (2006.01)
*B32B 37/02* (2006.01)
(Continued)

(52) U.S. Cl.
CPC .. *A61F 13/15723* (2013.01); *A61F 13/15699* (2013.01); *A61F 13/493* (2013.01);
(Continued)

(58) Field of Classification Search
CPC .......... A61F 13/15756; A61F 13/15723; A61F 13/5638; A61F 13/565; A61F 13/5655;
(Continued)

(56) References Cited

U.S. PATENT DOCUMENTS

2005/0148982 A1 7/2005 Van Gompel et al.
2006/0244166 A1 11/2006 Wada et al.
(Continued)

FOREIGN PATENT DOCUMENTS

CN 1575787 A 2/2005
EP 2 022 453 A1 2/2009
(Continued)

OTHER PUBLICATIONS

Co-pending U.S. Appl. No. 13/806,791, filed Dec. 24, 2012.
(Continued)

*Primary Examiner* — Linda L Gray
(74) *Attorney, Agent, or Firm* — Renner, Otto, Boisselle and Sklar, LLP

(57) ABSTRACT

The present invention relates to a disposable worn article, including: an absorbent body 2 including an absorbent core 24 which absorbs body fluid laminated between a liquid-permeable top sheet 26 and a liquid-impermeable back sheet 27; a pair of front flaps Ff extending in a girth direction X to be continuous with a front portion 20 of the absorbent body 2 that covers a front surface of a torso of a wearer; and a pair of back flaps Fb extending in the girth direction to be continuous with a back portion 21 of the absorbent body 2 that covers a back surface of the torso of the wearer, wherein: the front and back flaps Ff and Fb include a stretchable non-woven fabric 31 that stretches in the girth direction X; and an entire area of the absorbent core 24 is not essentially covered by the stretchable non-woven fabric 31.

3 Claims, 14 Drawing Sheets

(51) Int. Cl.
*A61F 13/15* (2006.01)
*A61F 13/493* (2006.01)

(52) U.S. Cl.
CPC .. *A61F 13/49011* (2013.01); *A61F 13/49014* (2013.01); *A61F 13/15756* (2013.01)

(58) Field of Classification Search
CPC ......... A61F 13/49014; A61F 13/49011; B32B 37/02; B32B 37/144; B32B 37/22; B32B 38/0004; B32B 38/1875; Y10T 156/13; Y10T 156/1067; Y10T 156/1077; Y10T 156/1087; Y10T 156/1097
See application file for complete search history.

(56) References Cited

U.S. PATENT DOCUMENTS

| | | | |
|---|---|---|---|
| 2009/0157034 | A1 | 6/2009 | Mattingly et al. |
| 2010/0051170 | A1 | 3/2010 | Nakakado |
| 2012/0253306 | A1 | 10/2012 | Otsubo et al. |

FOREIGN PATENT DOCUMENTS

| | | | |
|---|---|---|---|
| JP | 01-298202 | A | 12/1989 |
| JP | 04-144558 | A | 5/1992 |
| JP | 04-161152 | A | 6/1992 |
| JP | 6-77720 | U | 11/1994 |
| JP | 6-86725 | U | 12/1994 |
| JP | 6-86726 | U | 12/1994 |
| JP | 2004-357950 | A | 12/2004 |
| JP | 2007-105453 | A | 4/2007 |
| JP | 2008-36198 | A | 2/2008 |
| JP | 2009-202025 | A | 9/2009 |
| JP | 2011-136095 | A | 7/2011 |
| WO | WO 2004/054490 | A1 | 7/2004 |
| WO | WO 2008/126708 | A1 | 10/2008 |

OTHER PUBLICATIONS

International Search Report for corresponding International Application No. PCT/JP2011/066328 dated Oct. 25, 2011.
Chinese Office Action dated Oct. 30, 2014 for corresponding Chinese Application No. 201180034352.3 (with partial English translation).

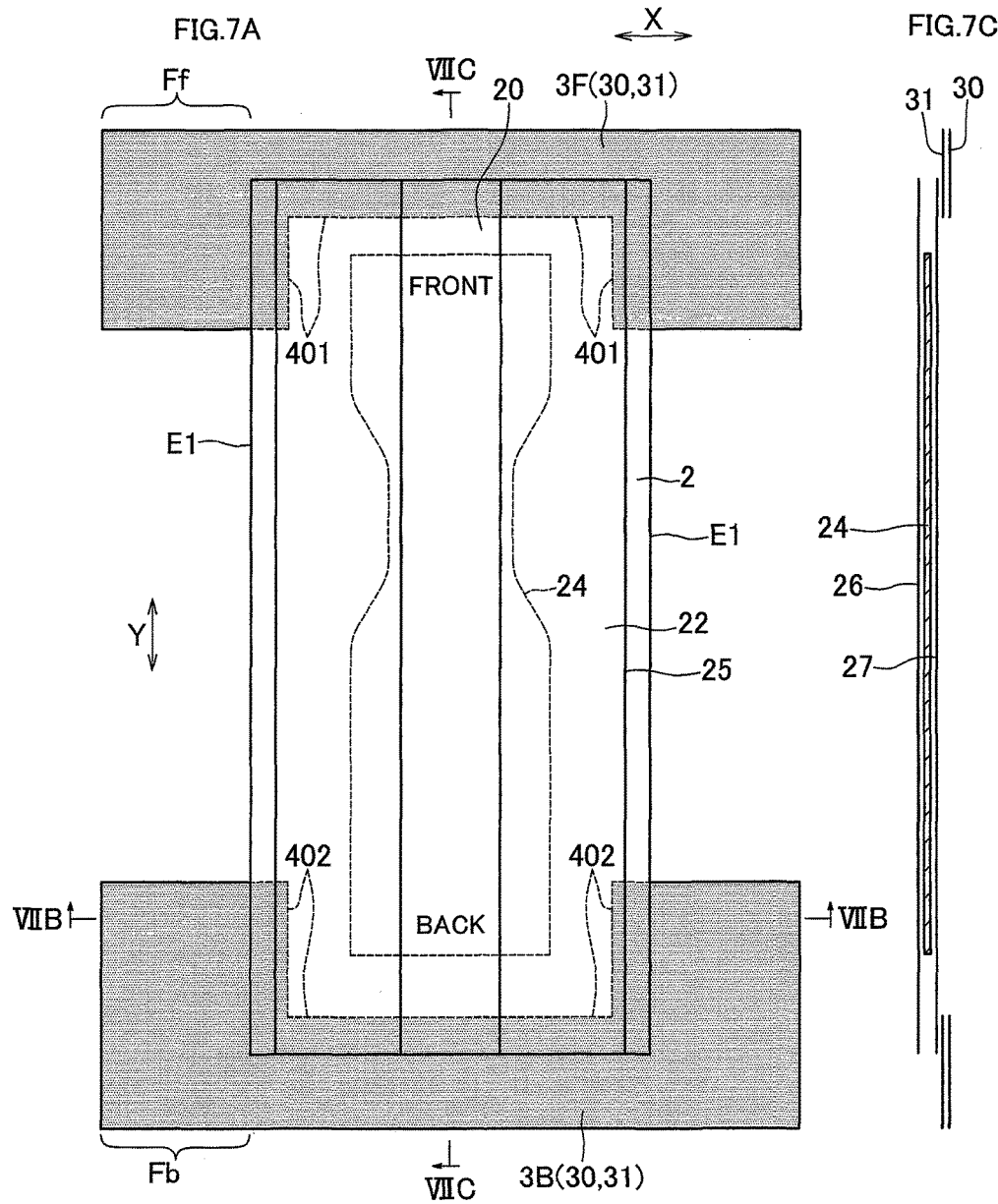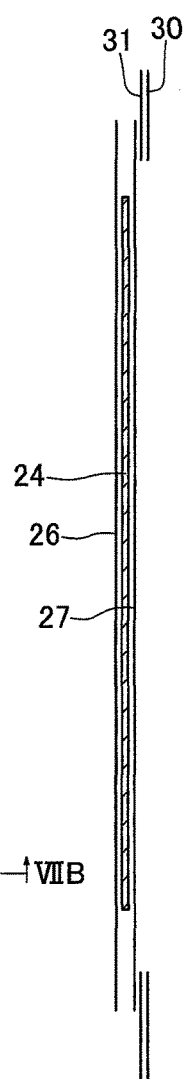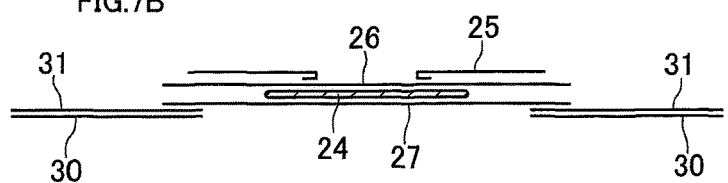

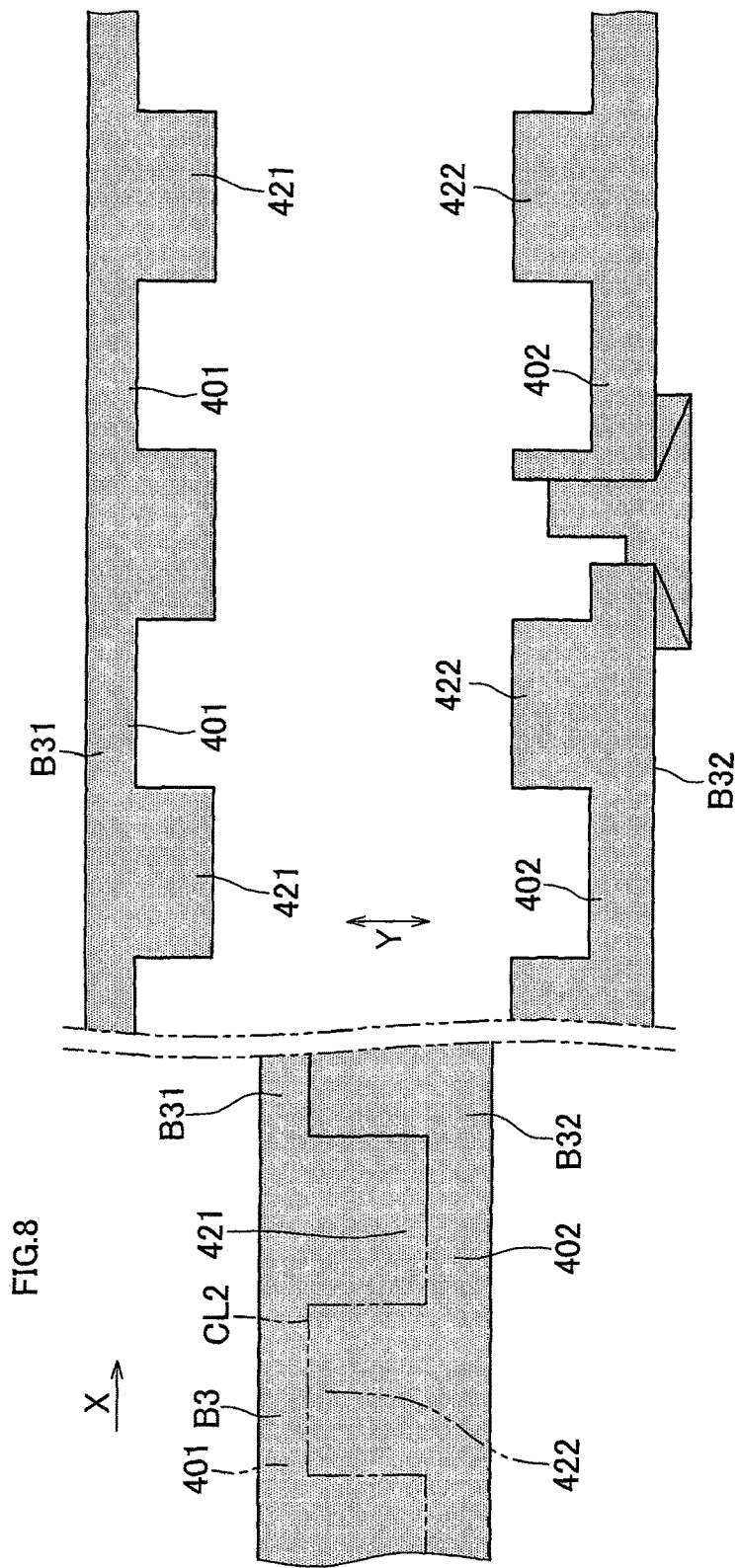

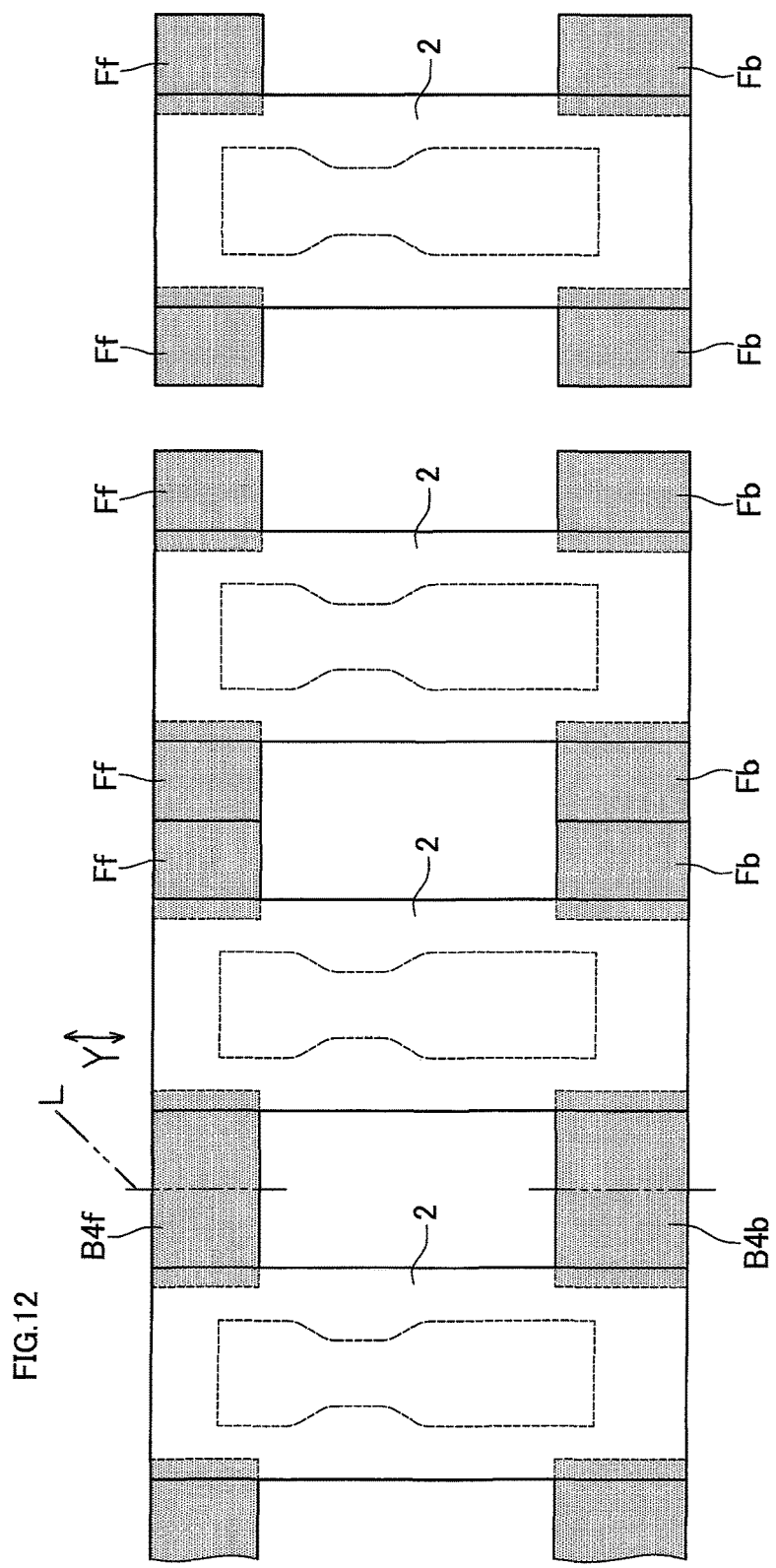

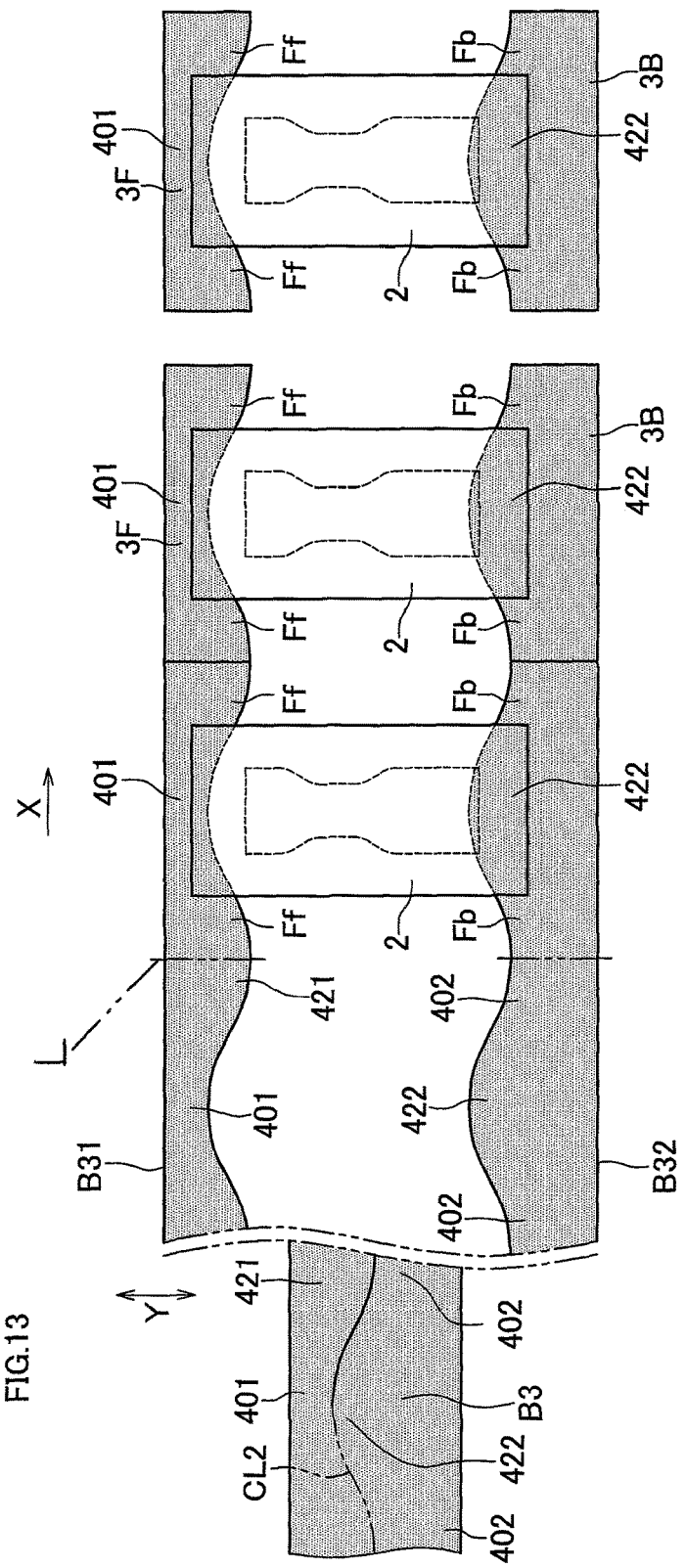

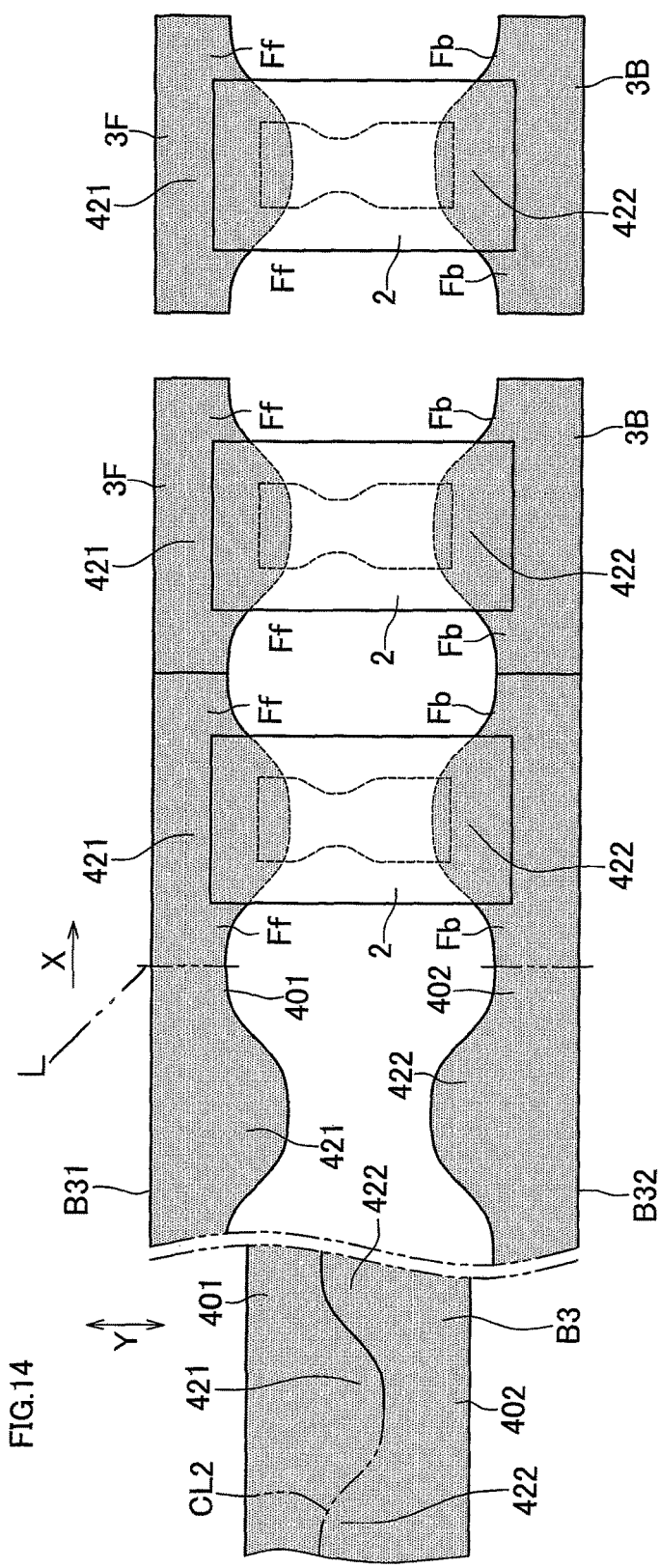

DISPOSABLE WORN ARTICLE AND METHOD FOR PRODUCING SAME

TECHNICAL FIELD

The present invention relates to a worn article using a non-woven fabric having a high stretchability, and a method for manufacturing the same.

BACKGROUND ART

Where a stretchability is given to a girth portion of a disposable worn article, typically, thread-shaped or band-shaped elastic members, being elongated, are fixed between two sheets of an essentially non-stretchable non-woven fabric with an adhesive therebetween. The elastic members shrink to form gathers in the girth portion.

In contrast, a method is known in the art in which a non-woven fabric having a high stretchability is layered on an essentially non-stretchable non-woven fabric to give a stretchability in the girth direction (see the first to third patent documents). The disclosure of three patent documents identified below is herein incorporated by reference.

CITATION LIST

Patent Literature

[First Patent Document] JP2004-357950 A (Abstract)
[Second Patent Document] JP2007-105453 A (Abstract)
[Third Patent Document] JP2009-202025 A (Abstract)

SUMMARY OF INVENTION

Technical Problem

However, when a stretchable non-woven fabric having a high stretchability is stretched in the girth direction, the stretchable non-woven fabric shrinks in the vertical direction perpendicular to the girth direction. When the tension in the girth direction is removed, the stretchable non-woven fabric, which has shrunk in the vertical direction, returns to the original dimension. Therefore, manufacturing errors are likely to occur in the worn articles. Moreover, a stretchable non-woven fabric has a high material cost, causing an increase in the cost of the product.

Thus, it is an object of the present invention to provide a disposable worn article using a non-woven fabric having a high stretchability and a method for manufacturing the same, with which manufacturing errors are unlikely to occur and the cost can be reduced.

Solution to Problem

A disposable worn article of the present invention includes: an absorbent body including an absorbent core which absorbs body fluid laminated between a liquid-permeable top sheet and a liquid-impermeable back sheet; a pair of front flaps extending in a girth direction to be continuous with a front portion of the absorbent body that covers a front surface of a torso of a wearer; and a pair of back flaps extending in the girth direction to be continuous with a back portion of the absorbent body that covers a back surface of the torso of the wearer, wherein: the front flaps and the back flaps each include at least one stretchable non-woven fabric that stretches in the girth direction; and an entire area of the absorbent core is not essentially covered by the stretchable non-woven fabric.

Advantageous Effects of Invention

With the present worn article, while the front and back flaps include a stretchable non-woven fabric, the entire area of the absorbent core is not essentially covered by the stretchable non-woven fabric. Therefore, when the stretchable non-woven fabric is stretched in the girth direction, the leg hole area of the absorbent core is unlikely to shrink in the vertical direction. Thus, manufacturing errors are unlikely to occur in the worn article.

Moreover, the proportion of the area of the stretchable non-woven fabric with respect to the entire worn article is small. Therefore, the cost can be reduced.

Note that a case where only the end of the absorbent core in the vertical direction is covered by the stretchable non-woven fabric is encompassed by the definition that the entire area of the absorbent core is not essentially covered by the stretchable non-woven fabric.

In the present invention, a stretchable non-woven fabric refers to a non-woven fabric having an elongation of 10% to 300% and having a mechanical (physical) property such that it restores its original shrunk state when a tensile stress is removed.

That is, the stretchable non-woven fabric refers to a non-woven fabric which does not essentially have a permanent strain at an elongation less than 10% and an elongation of 10% and which has a large elongation $\delta$ at the elastic limit.

While ordinary non-woven fabrics and resin sheets also stretch, they do not have the rubber elasticity. Therefore, when elongated by 10% or more, those non-woven fabrics will have an essentially permanent strain. Therefore, these non-woven fabrics are not stretchable non-woven fabrics but are essentially non-stretchable non-woven fabrics.

Herein, the elongation $\delta$(%) is defined by Expression (1) below.

$$\delta = 100\% * (LA - LB)/LB \qquad (1)$$

LA: Length of non-woven fabric after elongation
LB: Length of non-woven fabric before elongation The stretchable non-woven fabric may be a non-woven fabric manufactured, in advance outside the production line of the worn article, as a stretchable non-woven fabric that is stretchable in the longitudinal direction. Alternatively, the stretchable non-woven fabric may be a stretchable non-woven fabric whose stretchability is expressed by processing a non-stretchable continuous non-woven fabric during the manufacturing process of the worn article, or a stretchable non-woven fabric whose stretchability is improved by processing a low-stretchability continuous non-woven fabric.

The expression or the improvement of the stretchability can be realized by performing an inline process using a pair of rolls of which teeth and grooves mesh with each other, for example. More specifically, a band-shaped non-woven fabric including a non-elastic fiber layer integrally provided on both sides or one side of an elastic layer, made of an elastic fiber layer, a net-shaped elastic non-woven fabric, an elastic film, or the like, is taken into between the pair of rolls, thereby tearing the non-elastic fiber layer, elongating the constituent fibers or breaking thermally-welded points between fibers, thus obtaining a band-shaped non-woven fabric having a structure such that the stretching/shrinking of the elastic layer is unlikely to be inhibited. As the non-elastic fiber layer changes to a structure such that the stretching/shrinking of the elastic layer is unlikely to be inhibited, there is obtained a stretchable non-woven fabric with an expressed or improved stretchability.

Note that the stretchable non-woven fabric may have an anisotropy such that it elongates only in the girth direction and does not essentially elongate in the vertical direction.

On the other hand, the back sheet is formed by an essentially non-stretchable resin sheet, and the top sheet is formed by an essentially non-stretchable non-woven fabric. Herein, "non-stretchable" does not mean that it "does not elongate", but refers to a property that a permanent strain occurs in a material such that it cannot restore its original state or breaks when elongated by 10%; ordinary non-woven fabrics and sheets are non-stretchable.

A manufacturing method of the present invention includes the steps of obtaining a first and second laminate non-woven fabrics including pieces of the stretchable non-woven fabric arranged intermittently on a continuous non-woven fabric that is continuous in a longitudinal direction and is essentially non-stretchable while the pieces of the stretchable non-woven fabric are being elongated in the longitudinal direction; successively providing the absorbent bodies so as to span between a first portion of the first laminate non-woven fabric where the stretchable non-woven fabric is absent and a second portion of the second laminate non-woven fabric where the stretchable non-woven fabric is absent, while transferring the first and second laminate non-woven fabrics in parallel to each other and in the longitudinal direction; and cutting the first and second laminate non-woven fabrics along a virtual cut-off line extending in a width direction perpendicular to the longitudinal direction in areas of the first and second laminate non-woven fabrics between the absorbent bodies, so as to produce individual worn articles.

In this case, the stretchable non-woven fabric is arranged only in portions where the front and back flaps are formed. Therefore, manufacturing errors are unlikely to occur, and the cost will also be inexpensive.

When a stretchable non-woven fabric is attached to a non-stretchable continuous non-woven fabric, the stretchable non-woven fabric is typically set to a state where it is elongated by 10% to 300%. The elongation $\delta$ is preferably 20% to 200%, more preferably 50% to 180%, and most preferably 70% to 150%.

While the area of the laminate obtained by attaching the stretchable non-woven fablic to the non-woven fabrics shrinks by an amount accounting for the elongation in the attachment process, it will exert a shrinking force in the girth direction when worn, thereby fitting the worn article to the torso of the wearer.

Even if the stretchable non-woven fabric is a non-woven fabric having a desirable stretchability in the longitudinal direction thereof, the stretchable laminate (stretchable non-woven fabric) obtained by attaching it, while in its elongated state, on a non-stretchable non-woven fabric that does not essentially elongate, will not substantially elongate beyond its elongated state or the elongation will be rapidly inhibited after it is slightly elongated beyond the elongated state (so-called "saturation").

Another manufacturing method of the present invention includes the steps of: slitting a stretchable continuous non-woven fabric that is continuous in a longitudinal direction and is stretchable in the longitudinal direction along a predetermined wave-shaped cut-off line while carrying the stretchable continuous non-woven fabric in the longitudinal direction, thereby dividing the stretchable continuous non-woven fabric into a first continuous divided non-woven fabric having a first protruding portion and a first depressed portion, and a second continuous divided non-woven fabric having a second depressed portion and a second protruding portion; spacing apart the first continuous divided non-woven fabric and the second continuous divided non-woven fabric from each other; successively arranging the absorbent bodies so as to span between the first protruding portion of the first continuous divided non-woven fabric and one of the second depressed portion and the second protruding portion of the second continuous divided non-woven fabric, or successively arranging the absorbent bodies so as to span between the first depressed portion of the first continuous divided non-woven fabric and the other one of the second depressed portion and the second protruding portion of the second continuous divided non-woven fabric; and cutting off the first and second continuous divided non-woven fabrics along a cut-off line extending in a width direction perpendicular to the longitudinal direction between the absorbent bodies, so as to produce individual worn articles.

Another manufacturing method of the present invention includes the steps of: successively arranging the absorbent bodies intermittently on an essentially non-stretchable continuous non-woven fabric that is continuous in a longitudinal direction and has a pair of side edges; forming holes to be leg holes in the continuous non-woven fabric between the absorbent bodies; arranging the stretchable non-woven fabric, while being elongated in the longitudinal direction, intermittently along the pair of side edges extending along the longitudinal direction with the leg holes interposed therebetween; and cutting off the non-stretchable non-woven fabric between the absorbent bodies, so as to produce individual worn articles.

Also in this case, advantages similar to those of the manufacturing methods described above will be obtained.

Still another manufacturing method of the present invention includes the steps of: cutting off a stretchable continuous non-woven fabric that is continuous in a longitudinal direction and is stretchable in the longitudinal direction along a predetermined wave-shaped virtual cut-off line while carrying the stretchable continuous non-woven fabric in the longitudinal direction, thereby dividing the stretchable continuous non-woven fabric into a first continuous divided non-woven fabric having a first protruding portion and a first depressed portion, and a second continuous divided non-woven fabric having a second depressed portion and a second protruding portion; spacing apart the first continuous divided non-woven fabric and the second continuous divided non-woven fabric from each other; changing an arrangement relationship between the first continuous divided non-woven fabric and the second continuous divided non-woven fabric so that the first protruding portion and the second protruding portion oppose each other and the first depressed portion and the second depressed portion oppose each other; successively providing the absorbent bodies so as to span between the first depressed portion and the second depressed portion; and cutting off the first and second continuous divided non-woven fabrics along a virtual cut-off line extending in a width direction perpendicular to the longitudinal direction between the absorbent bodies, so as to produce individual worn articles.

When the absorbent body is provided so as to span (bridge) between the first depressed portion and the second depressed portion, the absorbent core will not be essentially covered by the first and second depressed portions.

Also in this case, advantages similar to those of the manufacturing methods described above will be obtained.

Another manufacturing method of the present invention includes the steps of: carrying a plurality of the absorbent bodies while the absorbent bodies are spaced apart from each other in the girth direction; providing a first stretchable non-woven fabric, which accounts for two of the front flaps, so as to span between absorbent bodies adjacent to each other in the girth direction, and providing a second stretchable non-woven fabric, which accounts for two of the back flaps, so as to span therebetween; and cutting off the first and second stretchable non-woven fabrics between the adjacent absorbent bodies so as to produce individual worn articles.

The stretchable non-woven fabrics provided so as to span between adjacent absorbent bodies are arranged so as not to overlap with the absorbent core.

Also in this case, advantages similar to those of the manufacturing methods described above will be obtained.

BRIEF DESCRIPTION OF DRAWINGS

FIG. 7A is a schematic plan view showing a worn article, unfolded, according to Embodiment 3 of the present invention, FIG. 7B is a cross-sectional view showing the same taken along line VIIB-VIIB, and FIG. 7C is a cross-sectional view taken along VIIC-VIIC.

FIG. 8 is a schematic plan view showing a method for manufacturing the worn article.

FIG. 12 is a schematic plan view showing a manufacturing step of the worn article.

FIG. 13 is a schematic plan view showing a method for manufacturing a worn article of Embodiment 4.

FIG. 14 is a schematic plan view showing a method for manufacturing a worn article of Embodiment 5.

DESCRIPTION OF EMBODIMENTS

Figure 1:
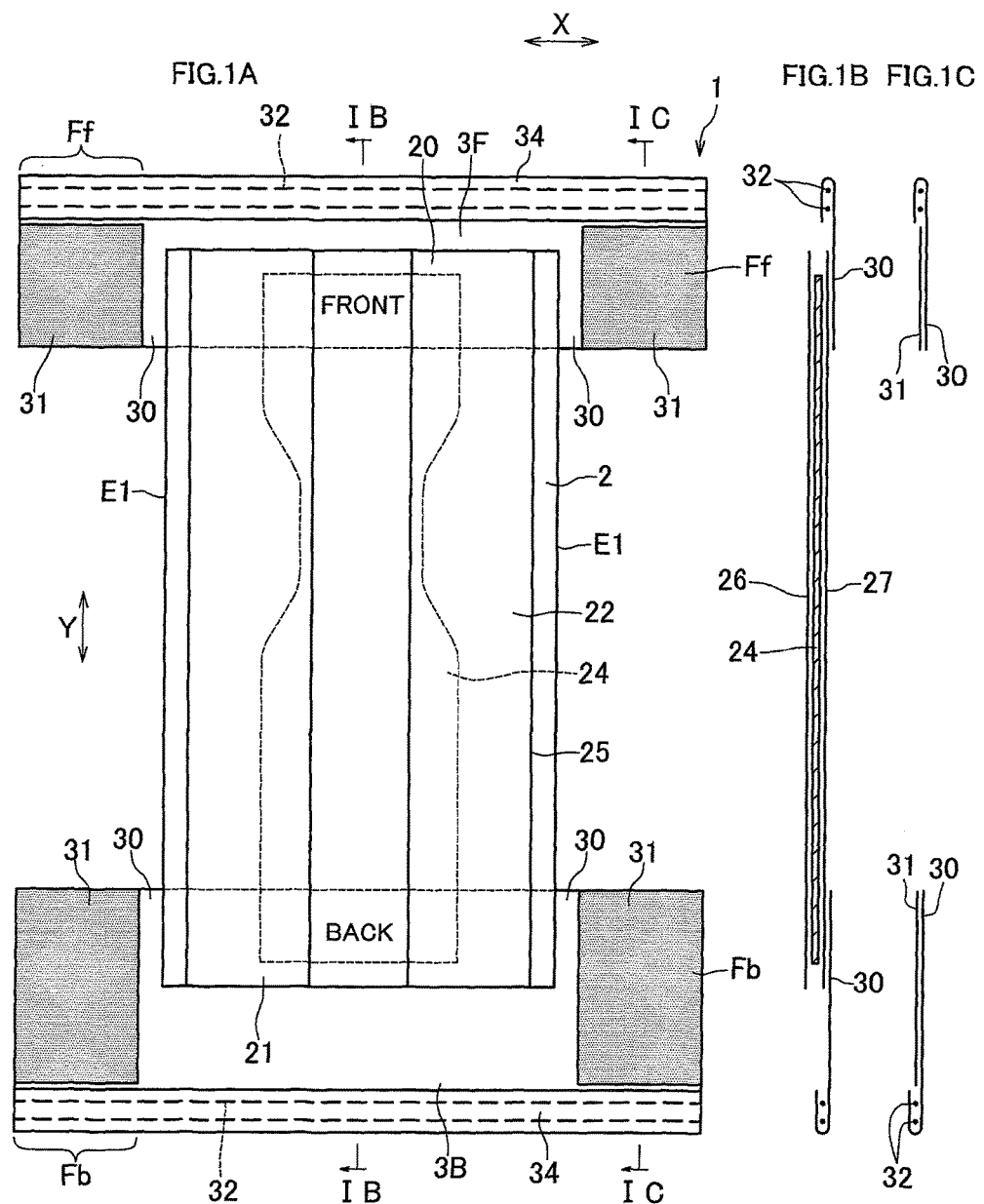
FIG. 1A is a schematic plan view showing a worn article, unfolded, according to Embodiment 1 of the present invention.
FIG. 1B is a cross-sectional view showing the same taken along line IB-IB.
FIG. 1C is an end view showing the same taken along line IC-IC.

The present invention will be understood more clearly from the following description of preferred embodiments taken in conjunction with the accompanying drawings. Note however that the embodiments and the drawings are merely illustrative, and should not be taken to define the scope of the present invention. The scope of the present invention shall be defined only by the appended claims. In the accompanying drawings, like reference numerals denote like components throughout the plurality of figures.

Embodiment 1

A structure of a worn article 1 according to Embodiment 1 of the present invention will now be described with reference to the drawings.

Figure 2:
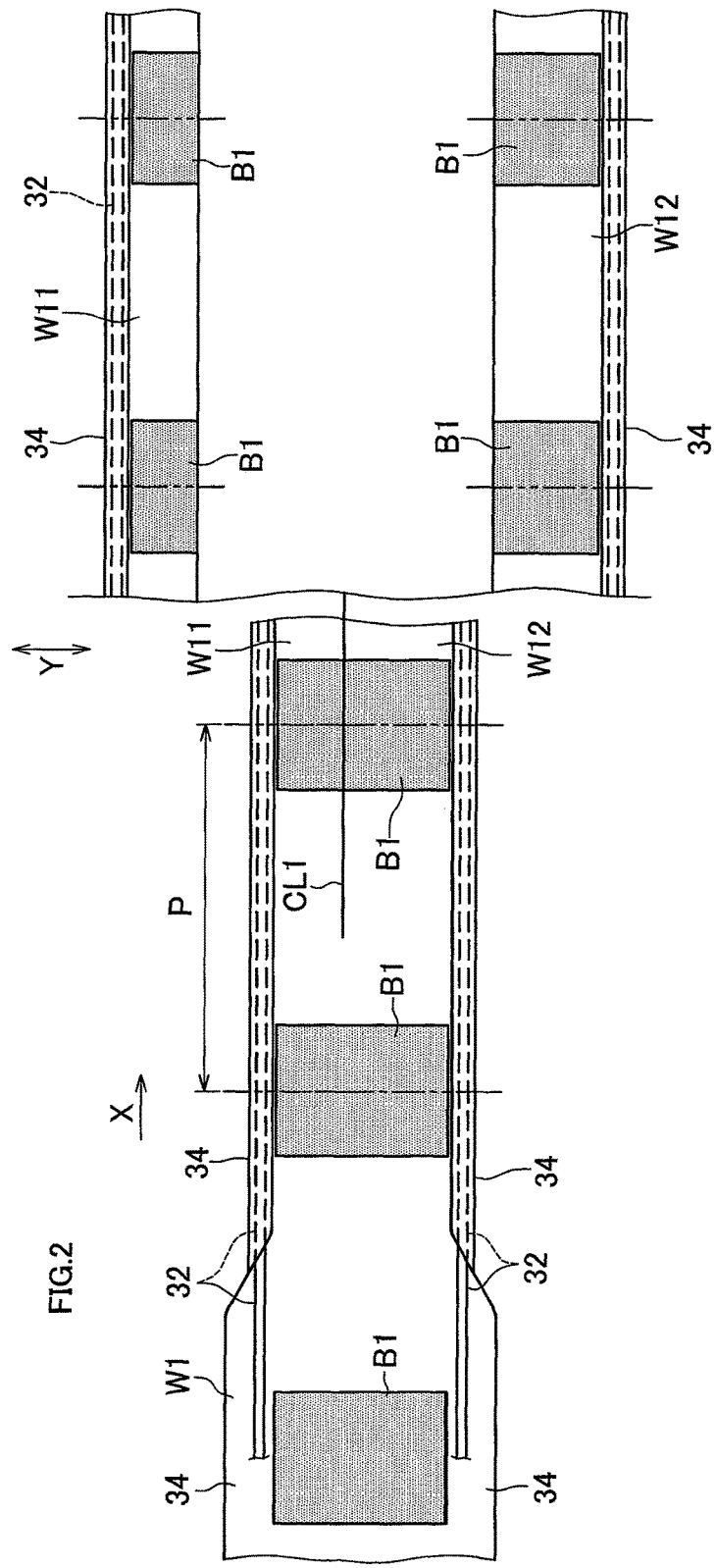
FIG. 2 is a schematic plan view showing a method for manufacturing the worn article.
Figure 3:
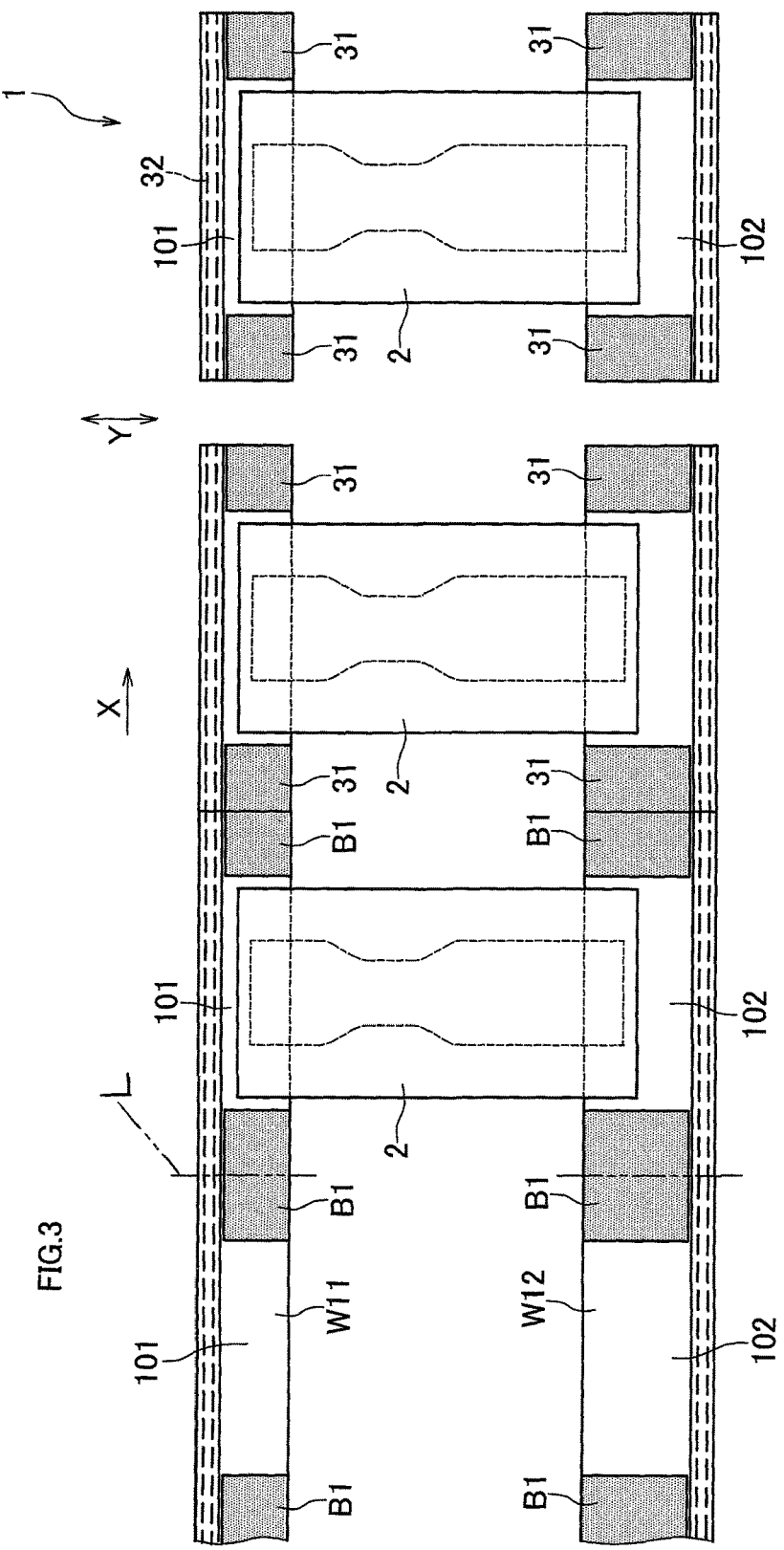
FIG. 3 is a schematic plan view showing a method for manufacturing the worn article.

FIGS. 1 to 3 show Embodiment 1.

As shown in FIGS. 1A to 1C, the worn article 1 of Embodiment 1 includes an absorbent body 2, a front girth member 3F, and a back girth member 3B. The absorbent body 2 includes a front portion (front girth portion) 20 covering the front torso of the wearer and extending in the girth direction X, a back portion (back girth portion) 21 covering the back torso of the wearer and extending in the girth direction X, and a crotch portion 22 covering the crotch of the wearer between the front portion 20 and the back portion 21.

The crotch portion 22 is continuous with the front portion 20 and the back portion 21, and extends in the vertical direction Y perpendicular to the girth direction X. The absorbent body 2 forms a part or whole of the crotch portion 22.

In FIG. 1A, when worn, the crotch portion 22 is folded in two along a line parallel to the girth direction X. Thus, end portions of the front girth member 3F and the back girth member 3B in the girth direction X overlap with each other.

As shown in FIG. 1A, an absorbent core 24 indicated by a broken line is provided on the absorbent body 2, and the absorbent core 24 absorbs body fluid. As shown in FIG. 1B, the absorbent core 24 is sandwiched between a top sheet 26 and a back sheet 27, and the sheets 26 and 27 and the absorbent core 24 are laminated on one another.

In FIG. 1B, the top sheet 26 is made of a liquid-permeable thin non-woven fabric, and covers the skin-contact surface of the absorbent core 24. A cuff 25 of FIG. 1A may be provided on the top sheet 26. The top sheet 26 of FIG. 1B is made of an essentially non-stretchable non-woven fabric.

In the present invention, the "skin-contact surface" refers to an inner surface that directly or indirectly contacts the skin of the wearer when the diaper is worn.

The back sheet 27 covers the non-skin-contact surface of the absorbent core 24, and is made of a liquid-impermeable resin sheet. An exterior non-woven fabric (not shown) may be bonded and laminated on the non-skin-contact surface of the back sheet 27. The resin sheet and the exterior non-woven fabric are essentially non-stretchable.

In the present invention, the "non-skin-contact surface" refers to an outer surface, opposite to the skin-contact surface, that does not contact the skin of the wearer when the diaper is worn.

In FIG. 1A, the absorbent body 2 is provided so as to span between the front girth member 3F and the back girth member 3B. That is, the front girth member 3F is attached to an end portion of the front portion 20 of the absorbent body 2 in the vertical direction Y. On the other hand, the back girth member 3B is attached to an end portion of the back portion 21 of the absorbent body 2 in the vertical direction Y.

The front and back girth members 3F and 3B form a pair of front flaps Ff and a pair of back flaps Fb, respectively, protruding from the absorbent body 2 in the girth direction X, and the flaps Ff and Fb each form a part of the front and back girth portions. That is, as shown in FIG. 1A, the flaps Ff and Fb protrude beyond the crotch portion 22 in the girth direction X, and extend beyond the opposing edges E1 of the absorbent body 2 (the crotch portion 22) in the girth direction X.

The front and back girth members 3F and 3B are obtained for example by laminating a pair of non-woven fabrics 30 and 31 shown in FIGS. 1A to 1C. These non-woven fabrics 30 and 31 are air-permeable.

In FIG. 1, an elastic member 32 for fitting the worn article 1 to the wearer may be provided on the front and back girth members 3F and 3B, as shown by broken lines of FIG. 1. The elastic member 32 may be, for example, a plurality of rubber threads or rubber tapes, a film, a material including a thermoplastic resin, or the like. The elastic member 32 may be made ineffective (left with no shrinking force) in the center of the front and the back.

The absorbent body 2 may include around-leg portions narrowed in conformity with the legs of the wearer. In areas continuous with the around-leg portion or the around-leg portion of the girth members 3F and 3B, an elastic member made of rubber threads may be provided, for example, so as to conform to around the legs of the wearer.

Where the worn article is a diaper, male touch fasteners (not shown) may be secured to the pair of back girth members 3B, whereas female touch fasteners may be secured to the front girth member 3F.

Note that a tape material with a fastening agent applied thereon may be used instead of a male touch fastener, in which case the front girth member 3F, etc., need to be provided with a surface to which the fastening agent easily adheres.

Where the worn article is a pants-type worn article, the end portions of the front flap Ff and the back flap Fb in the girth direction X may be welded together.

Next, an important part of the present embodiment will be described.

In the present embodiment, in portions of the front and back flaps Ff and Fb, the stretchable non-woven fabric 31 is attached on the non-stretchable non-woven fabric 30. The stretchable non-woven fabric 31 is not overlapping with the absorbent body 2, and is not overlapping with the non-stretchable non-woven fabric 30 in the end of the girth members 3F and 3B in the vertical direction Y (i.e., a side edge portion 34).

Note that in the figures, areas of the stretchable non-woven fabric 31 are dotted.

Next, a method for manufacturing the worn article of Embodiment 1 will be described.

As shown in FIG. 2, while a non-stretchable continuous non-woven fabric W1 is carried in the longitudinal direction X of the continuous non-woven fabric W1, a stretchable non-woven fabric B1 is arranged and attached intermittently on the continuous non-woven fabric W1.

The pitch P with which the stretchable non-woven fabrics B1 are arranged is equal to the length of the worn article 1 in the longitudinal direction (girth direction) X. When the stretchable non-woven fabric B1 is attached on the non-stretchable continuous non-woven fabric W1, the stretchable non-woven fabric B1 is attached while it is elongated in advance by 10% to 300% in the longitudinal direction X.

On the other hand, the elastic member 32 under a tension applied thereto is arranged along the longitudinal direction X on a pair of side edge portions 34 of the non-stretchable continuous non-woven fabric W1 while the non-stretchable continuous non-woven fabric W1 is folded back. Then, the non-woven fabrics W1 and B1 are cut off along the virtual cut-off line CL1 extending in the longitudinal direction X, thereby producing a first laminate non-woven fabric W11 and a second laminate non-woven fabric W12.

After the cut-off, the arrangement relationship between the non-woven fabric W11 and the non-woven fabric W12 in the width direction Y is changed so that the side edge portions 34 and 34 of the non-stretchable first and second laminate non-woven fabrics W11 and W12 are spaced apart from each other.

As shown in FIG. 3, after changing the arrangement, the absorbent bodies 2 are successively provided so as to span between a first portion 101 of the first laminate non-woven fabric W11 where the stretchable non-woven fabric B1 is absent and a second portion 102 of the second laminate non-woven fabric W12 where the stretchable non-woven fabric B1 is absent. After this arrangement, the first and second laminate non-woven fabrics W11 and W12 are cut off along the virtual cut-off line L extending in the width direction Y perpendicular to the longitudinal direction X in portions of the first and second laminate non-woven fabrics W11 and W12 between the absorbent bodies 2 and 2. Thus, individual worn articles 1 are obtained.

Note that the absorbent bodies 2 may be folded in two while the web is continuous before being cut off into individual worn articles 1.

Now, structures and manufacturing methods of worn articles 1 according to Embodiments 2 to 6 of the present invention will be described with reference to the drawings. The description below mainly discusses structures and methods that are different from those of Embodiment 1, and structures and methods similar to those of Embodiment 1 will not be described.

Embodiment 2

Figure 4:
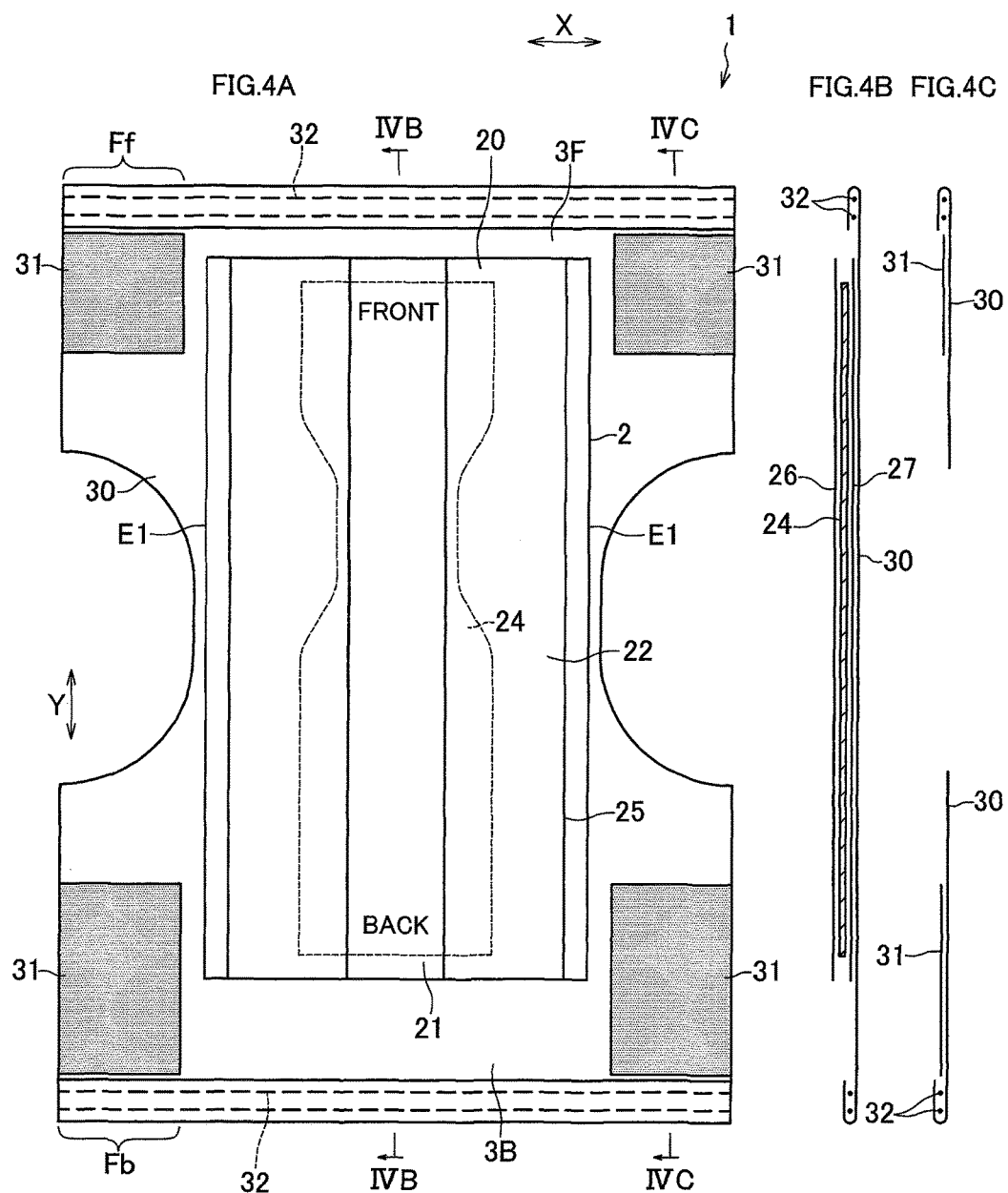
FIG. 4A is a schematic plan view showing a worn article, unfolded, according to Embodiment 2 of the present invention.
FIG. 4B is a cross-sectional view showing the same taken along line IVB-IVB.
FIG. 4C is an end view showing the same taken along line IVC-IVC.
Figure 5:
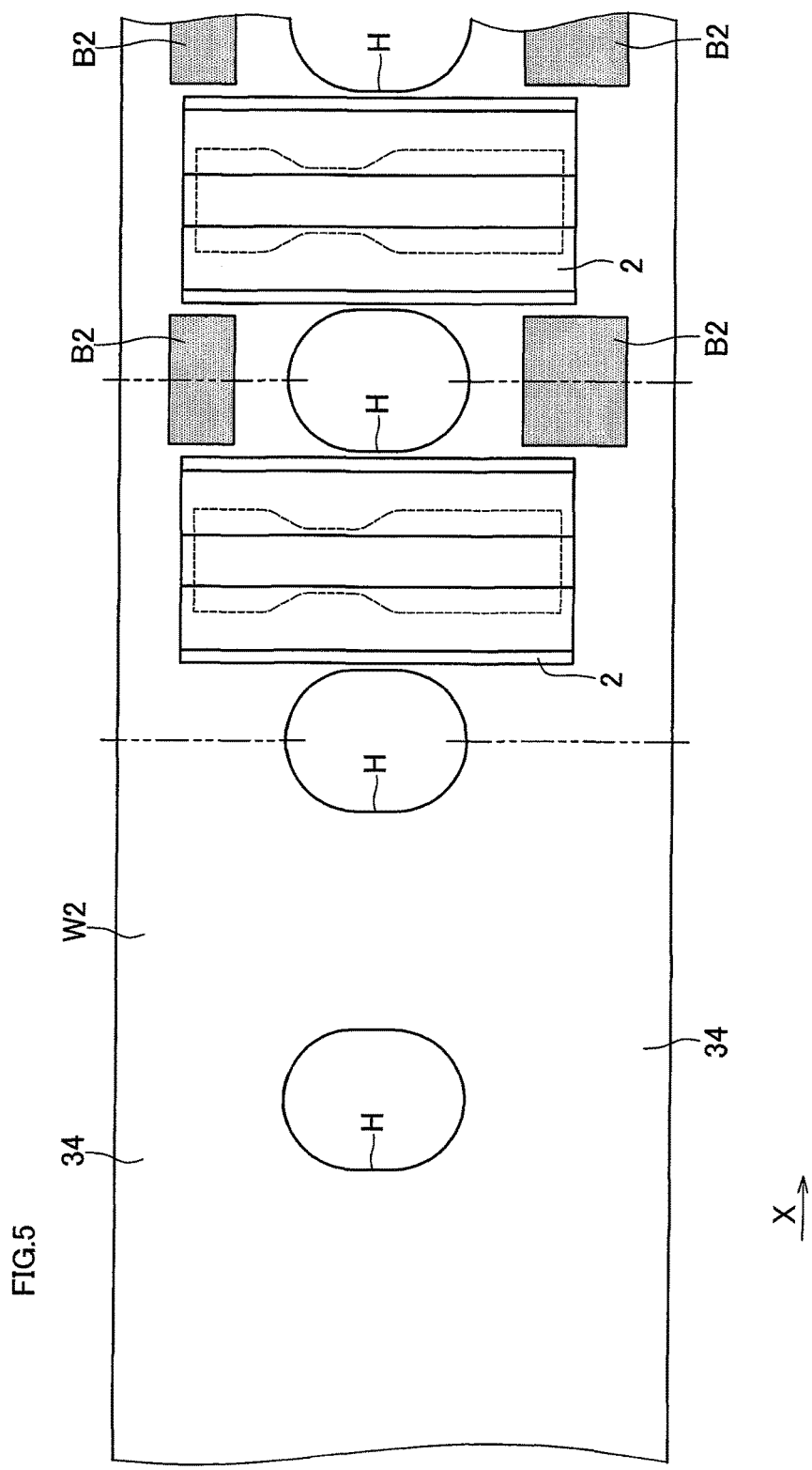
FIG. 5 is a schematic plan view showing a method for manufacturing the worn article.
Figure 6:
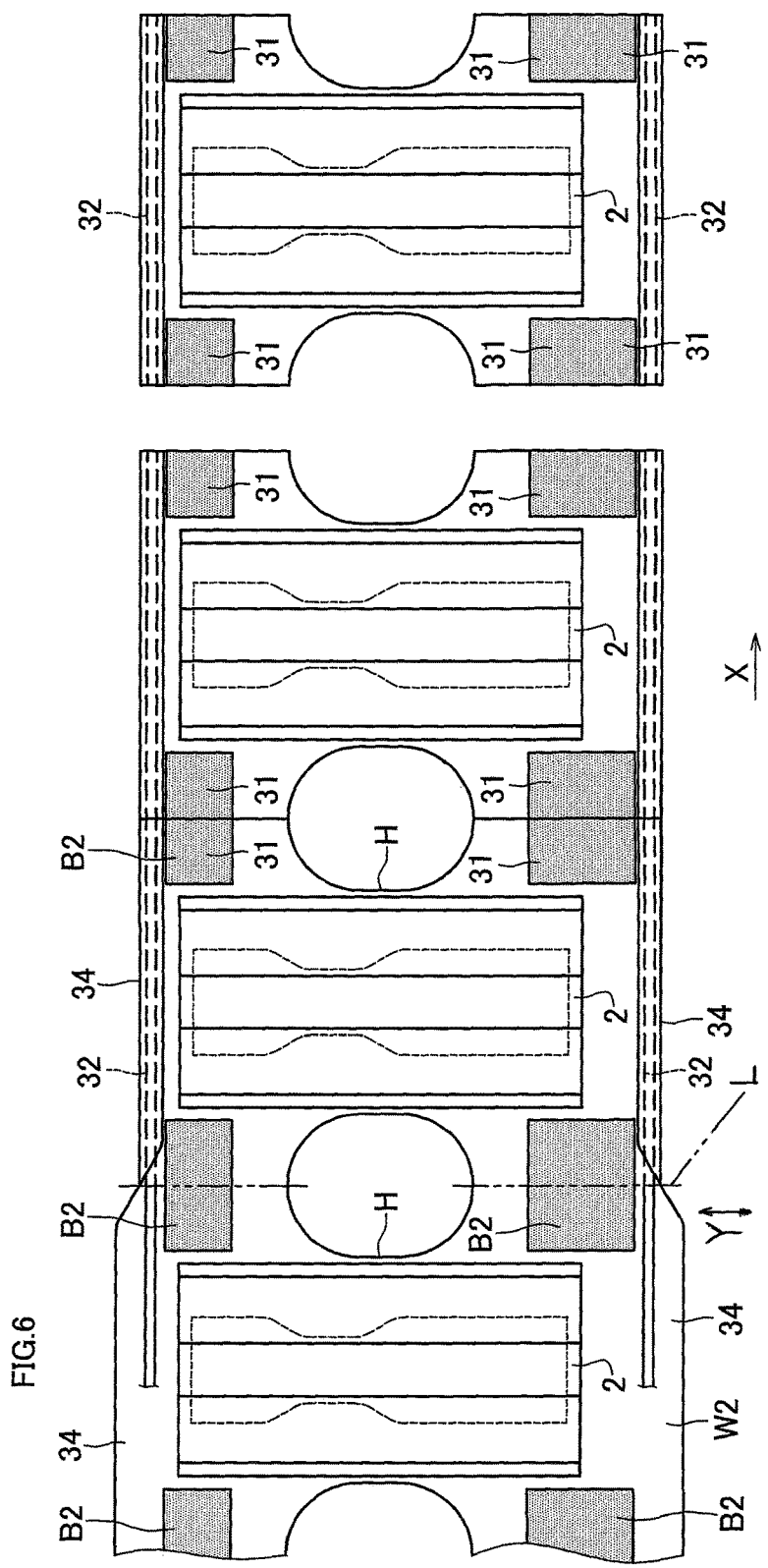
FIG. 6 is a schematic plan view showing a manufacturing step of the worn article.

FIGS. 4 to 6 show Embodiment 2.

In the present embodiment, the absorbent body 2 and four stretchable non-woven fabrics 31 are attached to one non-stretchable non-woven fabric 30 in which the around-leg portions are narrowed.

That is, the non-stretchable non-woven fabric 30 covers the back surface of the entire absorbent body 2, and the front girth member 3F and the back girth member 3B are formed to be continuous in the vertical direction Y with one non-stretchable non-woven fabric 30.

Next, a method for manufacturing the worn article 1 of Embodiment 2 will be described.

Holes H to be leg holes are successively formed intermittently on an essentially non-stretchable continuous non-woven fabric W2 that is continuous in the longitudinal direction X and has a pair of side edges 34 and 34. Then, the absorbent bodies 2 are successively arranged between the holes H and H formed in the non-stretchable continuous non-woven fabric W2.

On the other hand, the stretchable non-woven fabrics B2 and B2 are arranged, while being elongated by 10% to 300% in the longitudinal direction X, intermittently along a pair of side edges 34 and 34 that extend in the longitudinal direction X with the holes H to be leg holes interposed therebetween, thus producing a continuous laminate. While the stretchable non-woven fabrics B2 are each later cut in two as shown in FIG. 6 to produce the stretchable non-woven fabrics 31, the stretchable non-woven fabrics B2 may be arranged in advance so that each corresponds to a stretchable non-woven fabric 31.

As shown in FIG. 6, the elastic member 32 is arranged on a pair of side edges 34, and the side edges 34 are folded back.

Note that the order for the steps described above may be changed and, for example, they may be performed in the following order: the arrangement of the absorbent bodies 2; the arrangement of the elastic member 32; the formation of the holes H; and the arrangement of the stretchable non-woven fabrics B2.

Then, both of the stretchable non-woven fabric B2 and the non-stretchable continuous non-woven fabric W2 are cut off along the virtual cut-off line L extending in the width direction Y perpendicular to the longitudinal direction X between the absorbent bodies 2 and 2. Thus, individual worn articles 1 are cut off and produced from the continuous laminate.

Note that the continuous laminate may be folded in two before the worn articles 1 are cut off.

Embodiment 3

FIGS. 7A to 9 show Embodiment 3.

In Embodiment 3, the non-stretchable non-woven fabric 30 and the stretchable non-woven fabric 31 are laid on each other across the entire area of the front and back girth portions 3F and 3B of FIG. 7A in the girth direction, as shown in FIGS. 7B and 7C, but it may be formed only by the stretchable non-woven fabric 31.

The front and back girth members 3F and 3B each include the depressed portions 401 and 402 that are depressed at the center thereof in the girth direction X. The absorbent body 2 is provided so as to span between the edge portions of the pair of depressed portions 401 and 402, with the edge portion of the absorbent body 2 overlapping with the edge portions of the depressed portions 401 and 402.

Then, a method for manufacturing the present worn article 1 will be described with reference to FIGS. 8 and 9.

As shown in FIG. 8, the stretchable continuous non-woven fabric B3 forming the girth members 3F and 3B (FIG. 7A) is carried in the longitudinal direction X while the stretchable continuous non-woven fabric B3 is elongated in the longitudinal direction X. The continuous non-woven fabric B3 is slit along a rectangular wave-shaped cut-off line CL2 while carrying the non-woven fabric B3 in the longitudinal direction X. Thus, the continuous non-woven fabric B3 is divided into a first continuous divided non-woven fabric B31 including a first protruding portion 421 and the first depressed portion 401, and a second continuous divided non-woven fabric B32 including the second depressed portion 402 and a second protruding portion 422.

Then, the two continuous divided non-woven fabrics B31 and B32 are moved relative to each other in the width direction Y so as to space apart the first continuous divided non-woven fabric B31 and the second continuous divided non-woven fabric B32 from each other in the width direction Y perpendicular to the longitudinal direction X.

Then, the arrangement relationship between the first continuous divided non-woven fabric B31 and the second continuous divided non-woven fabric B32 in the longitudinal direction X is changed so that the first protruding portion 421 and the second protruding portion 422 oppose each other and the first depressed portion 401 and the second depressed portion 402 oppose each other. That is, the pair of continuous divided non-woven fabrics B31 and B32 are moved relative to each other by half the wavelength or (n+½) the wavelength (where n is a natural number) so that the depression/protrusion phases thereof are matched with each other.

Figure 9:
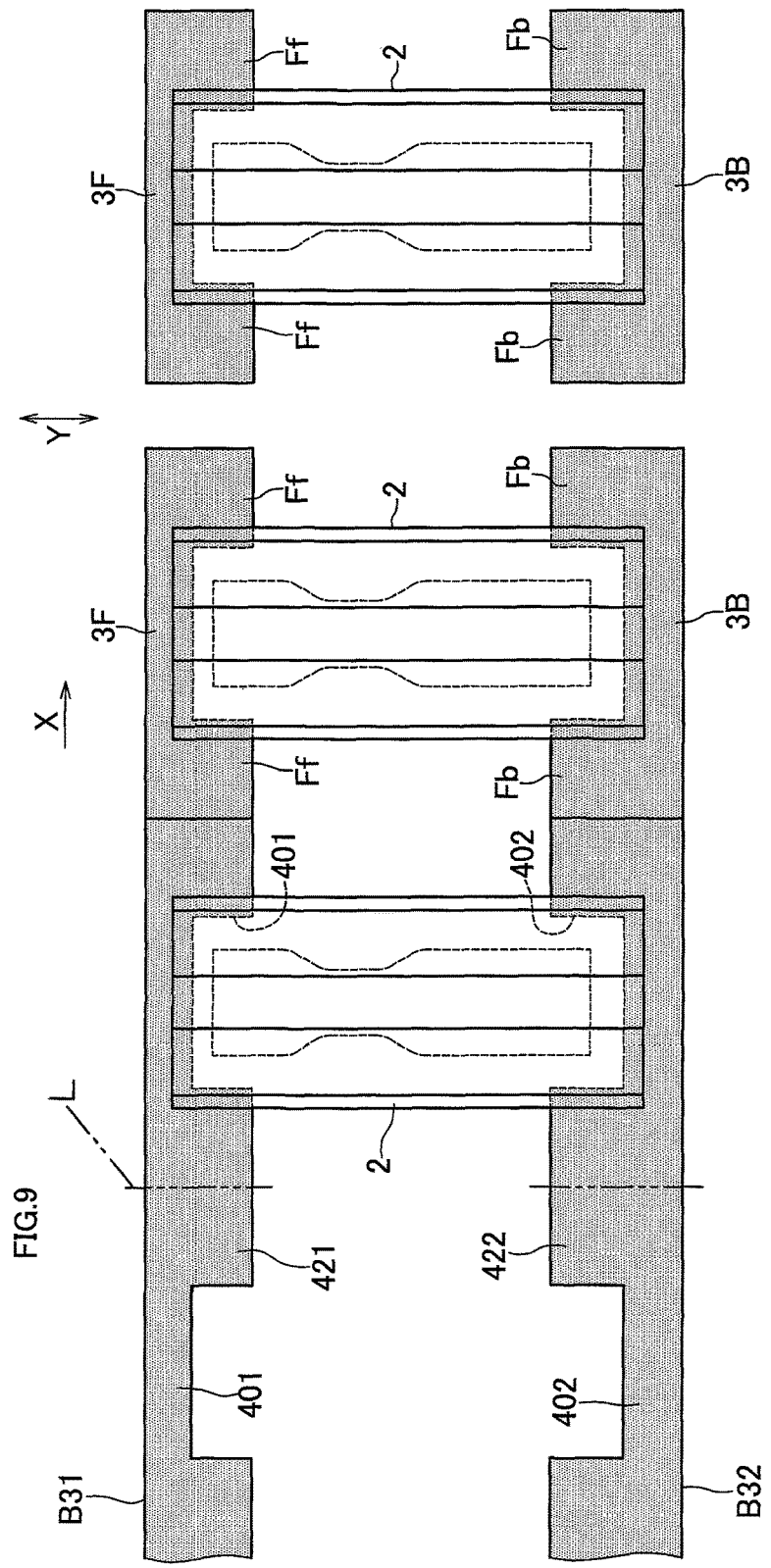
FIG. 9 is a schematic plan view showing a method for manufacturing the worn article.

As shown in FIG. 9, after changing the phase, the absorbent bodies 2 are successively arranged so as to span between the edge portions of the first depressed portion 401 and the second depressed portion 402 while the non-woven fabrics B31 and B32 are elongated at an elongation of 10% to 300% in the longitudinal direction X.

After the spanning provision, the non-woven fabrics B31 and B32 are cut off along the virtual cut-off line L extending in the width direction Y between adjacent absorbent bodies 2 and 2 so that the cut-off pieces each have a length of the individual worn article 1. Thus, the individual worn articles 1 are obtained in which the protruding portions 421 and 422 become the flaps Ff and Fb.

Note that the absorbent bodies 2 may be folded in two while the web is continuous before being cut off into individual worn articles 1.

In the present embodiment, the stretchable non-woven fabric B3 is attached to the non-stretchable non-woven fabric while the stretchable non-woven fabric is elongated in the longitudinal direction X, and therefore the stretchable non-woven fabric will have a reduced width before the attachment due to the elongation. Therefore, the width of the original fabric of the stretchable non-woven fabric is preferably about 110% to about 130% of the width of the original fabric of the non-stretchable non-woven fabric.

Embodiments 4 and 5

Next, a method for manufacturing worn articles 1 according to Embodiments 4 and 5 will be described.

In FIGS. 13 and 14, in Embodiments 4 and 5, the stretchable continuous non-woven fabric B3 is slit along a smooth wave-shaped virtual cut-off line CL2.

In FIG. 13, the pair of continuous divided non-woven fabrics B31 and B32 are not moved relatively to each other in the longitudinal direction X, and the protruding portion and the depressed portion are opposing each other. The absorbent bodies 2 are successively provided so as to span between the first depressed portion 401 and the second protruding portion 422.

Note that the other steps are similar to those of the third embodiment.

In FIG. 14, as in the third embodiment, after the pair of continuous divided non-woven fabrics B31 and B32 are slit along a smooth wave-shaped cut-off line CL2, they are moved relative to each other in the longitudinal direction X. The absorbent bodies 2 are successively provided so as to span between the first protruding portion 421 and the second protruding portion 422.

Note that the other steps are similar to those of the third embodiment.

Embodiment 6

FIGS. 10A to 12 show Embodiment 6.

Figure 10A:
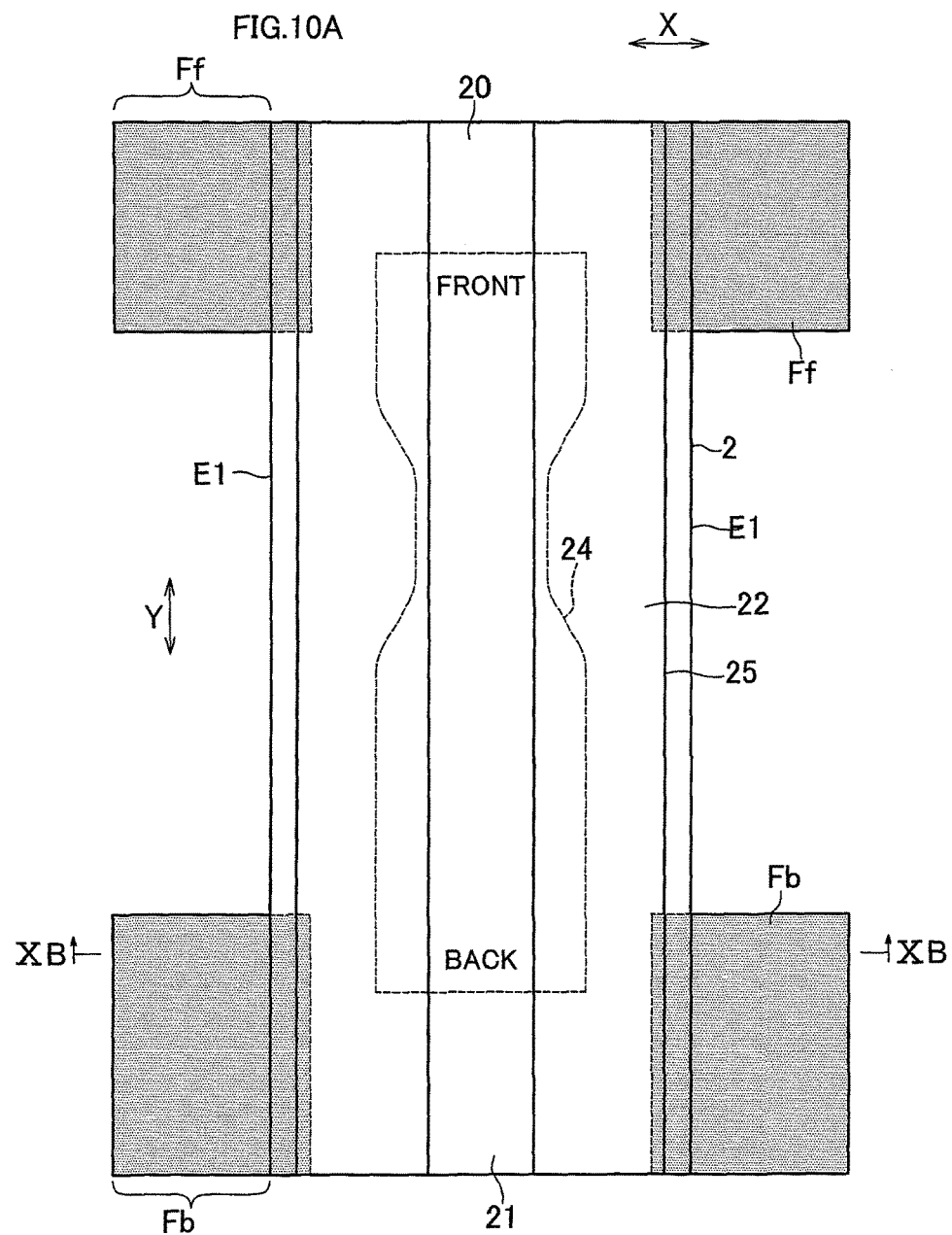
FIG. 10A is a schematic plan view showing a worn article, unfolded, according to Embodiment 6 of the present invention.
Figure 10B:
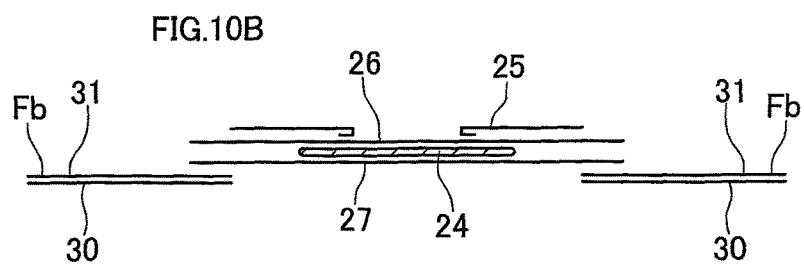
FIG. 10B is a cross-sectional view showing the same taken along line XB-XB.

In Embodiment 4, the front and back flaps Ff and Fb of FIG. 10A are secured so as to protrude in the longitudinal direction (girth direction) X from the edge portions of the absorbent body 2. That is, the flaps Ff and Fb are continuous with each other only via the absorbent body 2 therebetween. As shown in FIG. 10B, the flaps Ff and Fb are formed by a laminate including the non-stretchable non-woven fabric 30 and the stretchable non-woven fabric 31 laid on each other, but it may be formed only by the stretchable non-woven fabric 31.

Next, a method for manufacturing the worn article 1 of Embodiment 4 will be described with reference to FIGS. 11 and 12.

Figure 11:
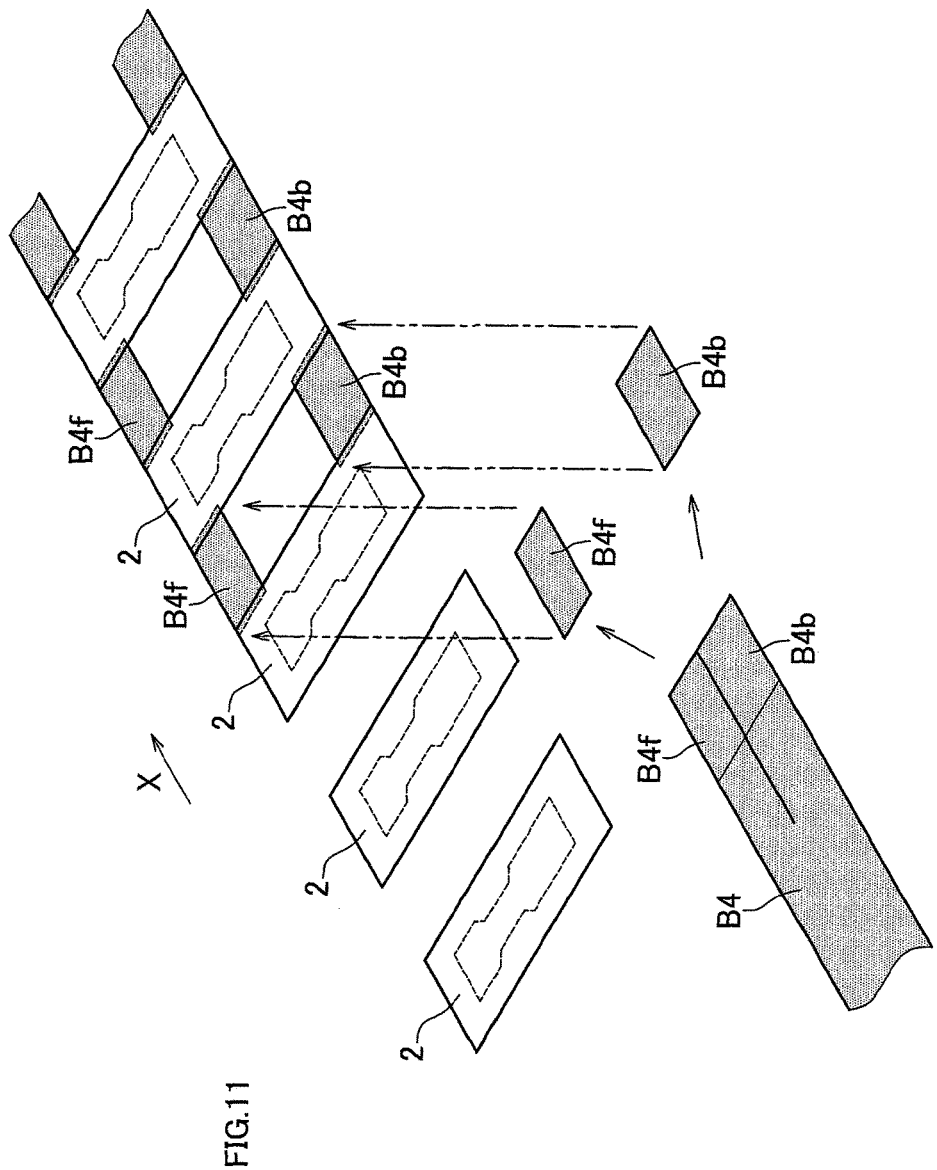
FIG. 11 is a schematic perspective view showing a method for manufacturing the worn article.

As shown in FIG. 11, while a plurality of the absorbent bodies 2 are carried while being spaced apart from each other in the girth direction X, a first stretchable non-woven fabric B4f which accounts for two of the front flaps Ff is provided so as to span between the absorbent bodies 2 and 2 adjacent to each other in the girth direction X and a second stretchable non-woven fabric B4b which accounts for two of the back flaps Fb is provided so as to span therebetween.

The stretchable non-woven fabrics B4f and B4b may be produced by, for example, slitting a single, band-shaped, long, continuous stretchable non-woven fabric B4 in two and cutting off the tip portion thereof. The stretchable non-woven fabrics B4f and B4b may be formed by laminating in advance a non-stretchable non-woven fabric with a stretchable non-woven fabric being elongated in the longitudinal direction X, or may be formed only by a stretchable non-woven fabric.

Then, as shown in FIG. 12, the first and second stretchable non-woven fabrics B4f and B4b are cut off along the virtual cut-off line L extending in the width direction Y between adjacent absorbent bodies 2 and 2. Thus, individual worn articles 1 are obtained.

Note that the cut-off may be done after the continuous laminate is folded in two.

INDUSTRIAL APPLICABILITY

The present invention is applicable to diaper-type and pants-type disposable worn articles and manufacturing methods therefor.

REFERENCE SIGNS LIST

1: Worn article
2: Absorbent body
20: Front portion
21: Back portion
24: Absorbent core
26: Top sheet
27: Back sheet
30: Non-stretchable non-woven fabric
31: Stretchable non-woven fabric
Ff: Front flap
Fb: Back flap
B1, B2, B3, B4: Stretchable non-woven fabric
W1, W2: Non-stretchable non-woven fabric

The invention claimed is:

1. A method for manufacturing a disposable worn article, the worn article including:
  an absorbent body including an absorbent core absorbing body fluid, the absorbent core laminated between a liquid-permeable top sheet and a liquid-impermeable back sheet;
  a pair of front flaps extending in a girth direction to be continuous with a front portion of the absorbent body that is adapted to cover a front surface of a torso of a wearer; and
  a pair of back flaps extending in the girth direction to be continuous with a back portion of the absorbent body that is adapted to cover a back surface of the torso of the wearer, wherein:
  the front flaps and the back flaps each include at least one stretchable non-woven fabric that stretches in the girth direction; and
  an entire area of the absorbent core is not covered by the stretchable non-woven fabric,
  the method comprising the steps of:
  carrying a non-stretchable continuous non-woven fabric for a girth area, from which the pair of front flaps and the pair of back flaps are formed, in a longitudinal direction, the non-stretchable continuous non-woven fabric being continuous in the longitudinal direction;
  laminating stretchable non-continuous non-woven fabrics, from which the pair of front flaps and the pair of back flaps are formed, on the continuous non-woven fabric for the girth area while being elongated in the longitudinal direction so that the stretchable non-continuous non-woven fabrics are arranged intermittently in the longitudinal direction of the continuous non-woven fabric for the girth area;
  cutting off the continuous non-woven fabric for the girth area, together with the stretchable non-continuous non-woven fabrics, along a virtual cut-off line extending in the longitudinal direction, after the lamination, thereby obtaining first and second laminate non-woven fabrics;
  successively providing absorbent bodies so as to span between a first portion of the first laminate non-woven fabric where the stretchable non-woven fabric is absent and a second portion of the second laminate non-woven fabric where the stretchable non-woven fabric is absent, while transferring the first and second laminate non-woven fabrics in parallel to each other and in the longitudinal direction; and
  cutting the first and second laminate non-woven fabrics along a virtual cut-off line extending in a width direction perpendicular to the longitudinal direction in areas of the first and second laminate non-woven fabrics between the absorbent bodies, so as to produce individual worn articles.

2. The manufacturing method according to claim 1, wherein the step of cutting the first and second laminate non-woven fabrics is carried out by cutting the first and second laminate non-woven fabrics together with the stretchable non-continuous non-woven fabrics along the virtual cut-off line extending in the width direction in the areas of the first and second laminate non-woven fabrics between the absorbent bodies.

3. The manufacturing method according to claim 2, each of the stretchable non-continuous non-woven fabrics is cut into four pieces by the two steps: (i) the step of cutting off the continuous non-woven fabric for the girth area cutting, along the longitudinal direction, each of the stretchable non-continuous non-woven fabrics into two pieces; and (ii) the step of cutting the first and second laminate non-woven fabrics cutting, along the width direction, each of the two pieces into two pieces.

* * * * *